United States Patent [19]

Lafferty et al.

[11] Patent Number: 4,892,279

[45] Date of Patent: * Jan. 9, 1990

[54] FULLY PORTABLE MEDICAL I.V. EQUIPMENT STAND/POLE

[75] Inventors: William G. Lafferty; Robert E. Howard, both of Deephaven, Minn.

[73] Assignee: Polymedical Technologies, Inc., Deephaven, Minn.

[*] Notice: The portion of the term of this patent subsequent to Nov. 9, 2005 has been disclaimed.

[21] Appl. No.: 45,329

[22] Filed: May 4, 1987

[51] Int. Cl.$^4$ ............................................. A47G 29/00
[52] U.S. Cl. .................................... 248/125; 248/171; 248/411
[58] Field of Search ............... 248/125, 129, 124, 171, 248/434, 411, 404, 631, 169

[56] References Cited

U.S. PATENT DOCUMENTS

| | | | |
|---|---|---|---|
| 2,303,978 | 12/1942 | Biberman | 248/171 |
| 2,706,653 | 4/1955 | Blakely | 248/124 X |
| 2,957,187 | 10/1960 | Raia | 248/125 |
| 3,143,332 | 8/1964 | Watlington | 248/404 |
| 4,332,378 | 6/1982 | Pryor | 248/125 X |
| 4,360,281 | 11/1982 | Alsup, Jr. et al. | 248/411 X |
| 4,383,252 | 5/1983 | Purcell et al. | 248/124 X |
| 4,511,157 | 4/1985 | Wilt, Jr. | 248/125 X |

FOREIGN PATENT DOCUMENTS 1224721  6/1960  France ............................... 248/124

Primary Examiner—David L. Talbott

[57] ABSTRACT

Disclosed is a fully portable medical I.V. equipment stand/pole (12). This invention is a triple sectioned telescoping mast assembly (13),(14),(15), with each section able to be locked into the other by means of an internal rotary cam-clutch (16),(17),(18),(19), which maintains a desired height of I.V. fluid or feeding solution above the patient regardless if the patient is ambulatory or in bed. Opening or closing of the I.V. equipment stand/pole is accomplished with a single movement of a control handle(24) which controls the mast assembly support legs(23). Fluids and feeding solutions are hung from the hanger rod assembly (30,),(31),(32). A control knob (32) frees or restricts horizontal movement of the hanger rods (30), and the circular rotation of the entire assembly (30),(31),(32).

4 Claims, 2 Drawing Sheets

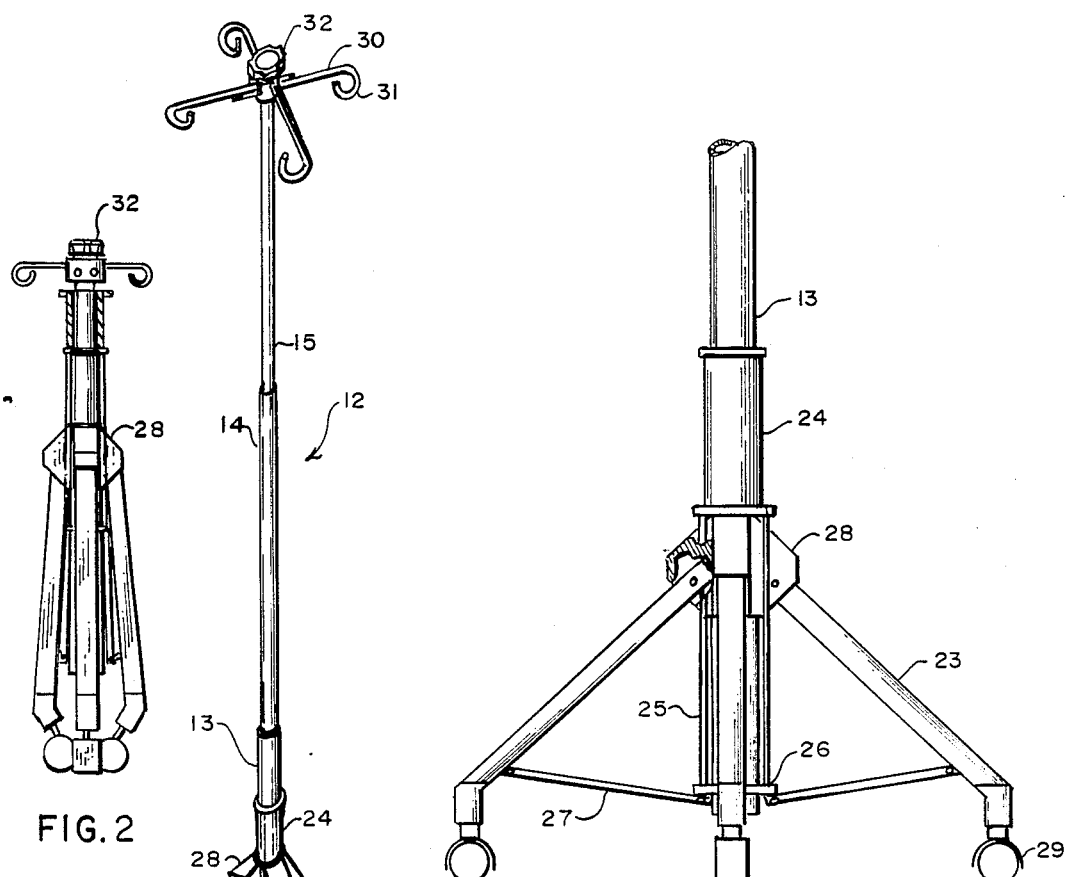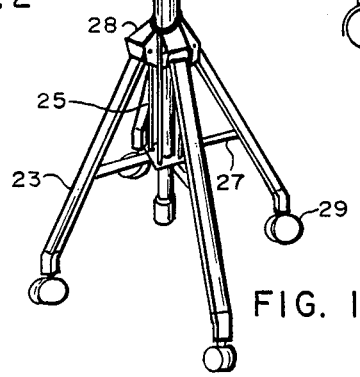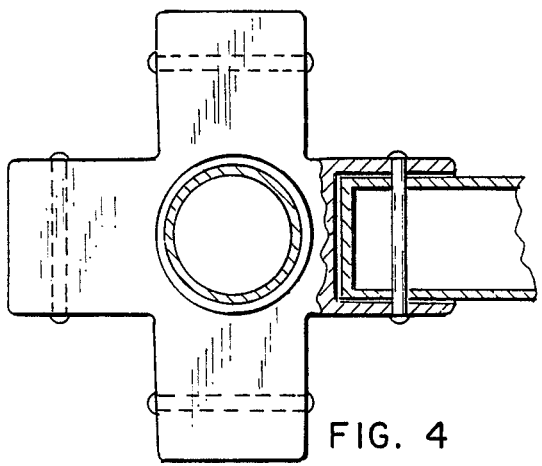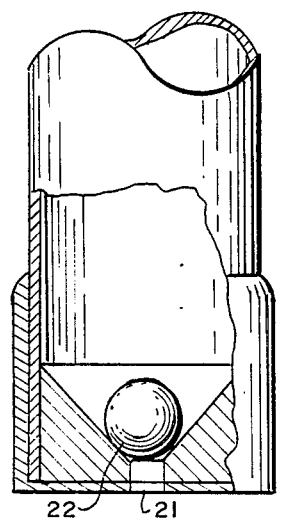

FULLY PORTABLE MEDICAL I.V. EQUIPMENT STAND/POLE

BACKGROUND OF THE INVENTION

1. Field of the Invention

The present invention relates to a medical I.V. infusion equipment device, and more particularly, to a fully portable; one piece I.V. equipment stand or pole which may be extended during use by a person in order to provide a primary means of support for medical infusion therapy; respiratory therapy; and critical care monitoring, devices.

2. Discussion of Related Technology

Many I.V. stands/poles have been developed which are designed to allow the hanging of intravenous fluids and fluid lines, and permit the attachment of parenternal and enteral IV flow controllers and pumps. Additionally, they are commonly used for the attachment of pulmonary ventilation equipment and bedside life function monitors in the critical care environments. Such devices are designed for institutional applications and an environment where the stand/pole remains on a given floor and is stored in a room designated for equipment storage. These devices are mostly designed as a single pole or telescoping two section pole, mounted on a swivel base with casters. If the pole is designed with telescoping sections, the sections may be fixed in place by the user by tightening a screw knob which is threaded through the larger outer section and which presses on the inner section to fix the two sliding sections and keep them from collapsing. Such poles come with a fixed two or four, I.V. bag hanging support on their tops.

There are several drawbacks of conventional I.V. stands/poles; they are very heavy (usually over 25 lbs.), difficult to store and transport; they present an unappealing mechanical appearance when used in the home or in nursing homes; and their low centered swivel base makes them extremely difficult for the patient or medical professional to walk with without tripping; if the telescoping sections of a multi-sectioned pole come loose, there are no protective mechanisms which will prevent the weight of the upper section along with any equipment attached to it from crashing downward and possibly injuring the patient; the external telescoping pole locking knob, because it is mounted on the side of the pole, tends to tangle the I.V. tubing which hangs from above.

Additionally, conventional I.V. stands/poles must be shipped by the manufacturer in two separate packages. The over six-foot length of single section I.V. poles is such that they are regularly prone to shipping damage and additional shipping costs.

SUMMARY OF THE INVENTION

The present invention is designed as a medical I.V. equipment stand/pole which addresses many of the difficulties present in prior I.V. stand/pole devices.

The general purpose of the present invention, which will be subsequently described in greater detail, is to provide an I.V. equipment stand/pole which is portable and able to be conveniently stored; and provide a safe walk-along device able to have attached to it many different kinds of critical health care devices for convenience to the patient and the health care professional.

In its preferred form, the fully portable, medical I.V. equipment stand/pole includes a central three section mast with interior cam-clutch section locking technology. The lowest section acts as a pneumatic piston, by way of an upper positioned seal and a lower positioned check valve. This inhibits the sudden fall of the two upper segments, should the middle section, to which equipment is attached, be accidentally loosened. The slow bleed of air from this internally designed piston, allows for a safe and smooth lowering the two upper sections.

The opening and closing of the base of this invention is accomplished in a single movement with a control handle which slides on the lower section of the mast and raises or lowers the lower leg supports while simultaneously opening or closing the four castered main support legs. The leg supports offer the advantage of ease of operation and secure locking of the legs in the open position so that they cannot be accidentally collapsed inwardly when the invention is in use. The user simply places one hand around the control handle, and another hand on any pole mast section. He then pulls up on the control handle to collapse the support legs of the pole. To open the pole, he does the reverse and pushes the control handle down toward the base of the pole invention. The control handle provides a space where the manufacturer can print his trademark or other writing such as instructions.

The invention also includes a rotating hanger rod assembly with horizontally sliding hanger rods which permit positional adjustment of up to four I.V. or eternal feeding bags. The movements of hanger rotation as well as the sliding hanger rods themselves is dependent on the opening or closing of a hanger control knob on the very top of the I.V. stand/pole.

The device is capable of being used for a variety of different applications in a variety of different environments. These features along with other advantages will become subsequently apparent, based on the details of construction and operation as more fully described hereinafter, reference being made to the accompanying drawings, wherein like numerals refer to like parts throughout.

BRIEF DESCRIPTION OF THE DRAWINGS

FIG. 1 is a perspective view of the present invention illustrating the invention in the fully opened position.

FIG. 2 is a perspective view of the device shown in FIG. 1 in the fully closed position.

FIG. 3 is a fragmentary side view of the the lowest mast section along with the sliding control handle and the attached leg assembly.

FIG. 4 is a top fragmentary view of the upper leg support mounting bracket.

FIG. 5 is a fragmentary view of the bottom of the lower mast section cutaway to show the piston check valve assembly.

DETAILED DESCRIPTION OF THE PREFERRED EMBODIMENT

Figure 11:
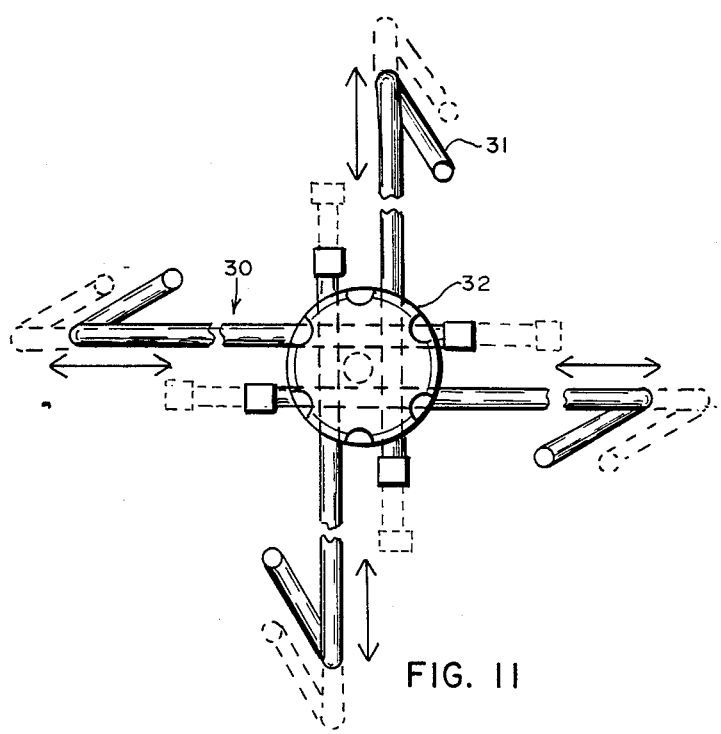
FIG. 11 is fragmentary view of the top of the hanger rod assembly showing direction of rod movement and locking control knob.

The embodiment shown and described herewithin has been reduced to practice, tested, received FDA market release approval, and has performed in an absolutely satisfactory manner.

The fully portable medical I.V. equipment stand/pole invention, generally designated by the reference number 12, is shown fully opened and extended in FIG. 1. The invention is composed of a three tubular segmented pole mast assembly with lower 13, middle 14, and upper 15 sections. The upper section telescoping into the middle, and the middle telescoping into the lower.

In the preferred embodiment, the middle mast section 14 is a tubular structure with nearly double the wall thickness of the of the upper and lower sections. This thickness prevents damage and denting from the attachment of any of the variety of conventional I.V. pumps and infusion controllers which generally use a locking bolt arrangement.

The upper and middle sections of this mast assembly lock in position to each other with a simple 90 degree clockwise rotation. An internal rotary cam-clutch assembly FIGS. 6,7,8, and 9 securely fixes the telescoping sections which allows one to maintain the overall height of the invention. With gravity flow of parenteral and enteral infusions in particular, height of the fluid source relative to the patient is critical. Additionally, for the first time, because of the invention's triple sectioned mast assembly, it is now possible to adjust the elevation of the fluid source without simultaneously changing the height of the fluid controlling device, such as an i.v. controller, which would be attached to the middle section 14. This will result in more accurate flow rates to the patient.

Figure 7:
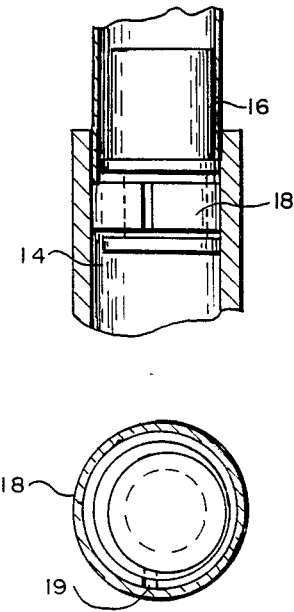
FIG. 7 is a side fragmentary and top cutaway perspective of the locking cam-clutch used to secure the position of the middle and upper mast sections.
Figure 8:
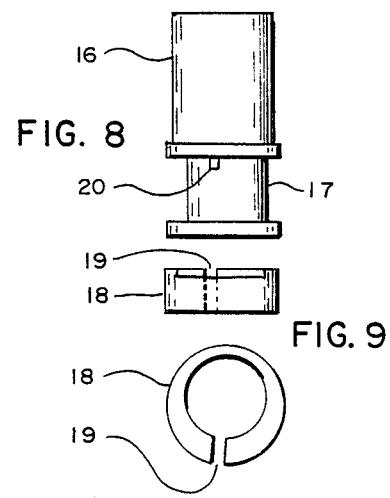
FIG. 8 is a side perspective of the locking cam-clutch, minus the clutch expansion ring.
Figure 9:
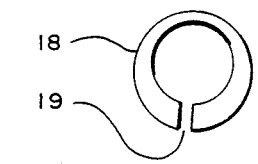
FIG. 9 is a side and also a top perspective of the expandable clutch ring.

Tightly fitted and permanently attached to the inside of the bottom end of the upper tubular section 15, is a rotary cam-clutch FIG. 7, 8 and 9. The clutch assembly is comprised of a molded body 16 and a molded channel 17 at its base. A non-concentric molded collar or ring 18 with a split opening 19 is positioned inside the channel 17, and acts as a non-concentric cam. The split opening 19 of the ring fits in such a way as to allow a molded tab 20 which is part of the molded channel design, to act as a ring expansion device. Because the ring is a non-concentric cam, when the upper mast section 15 is turned clockwise, the limiting inside diameter of the center section 14 forces the entire clutch and hence the upper section to bind into the center section. A movement in the counterclockwise direction of the upper section 15 against the center section 14 causes the cam-clutch to break free and release the two sections, allowing them to telescope.

Figure 6:
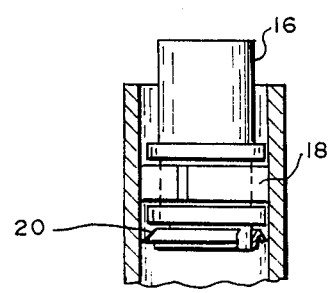
FIG. 6 is a cutaway fragmentary view of the top of the lower mast section showing the upper piston seal which is attached to the cam-clutch assembly of the middle mast section.

The rotary cam-clutch at the bottom of the center section FIG. 6 allows the center section to telescope into the lower section 13 and operates the same as that which is described above. Additionally, however, there is a downwardly sloping seal 20 which is attached to the bottom of the rotary cam-clutch. This seal prohibits any movement of air out of the top of the lower mast section.

In the preferred embodiment, at the bottom of the lower section 13, is a check valve FIG. 5. The action of this valve is one way, allowing air to rapidly pass up through an orifice 21 at the base of the lower section into the lower section as the center and upper mast sections 14 and 15 are telescoped upward. A gravity positioned ball 22 covers the orifice of the valve assembly and in combination with the seal 20 positioned in the top portion of thelower section, produces significant compressive back pressure to limit the speed of downward travel of the upper two sections into the lower section 13. The design is such that the greater the downward force, the greater the the compressive back pressure becomes in the lower section to compensate for that force, and hence a controlled lowering of the sections takes place. In a patient environment, it is critical that any I.V. pole not collapse should the telescoping locking device become accidentally loosened. It is believed that the pneumatic safety device built into this invention is unique and will offer improved patient safety.

The entire mast assembly is supported by four legs 23 which attach to the lower mast section 13 by means of a sliding control handle 24 shown in FIGS. 1, 2, and 3. The uniqueness of the leg and control handle assemblies is that it allows a single one-handed motion to open or close the supporting base of the entire invention.

The slidable control handle 24 has four connecting rods 25 attached to its base which extend vertically from the control handle to a slidable baseplate 26 located at the bottom of the lower mast assembly section as viewed when the invention is in the legs open position. Connected and hinged on that baseplate 26 are four nearly horizontal lower leg supports 27 viewed in FIG. 1 and 3. The opposite ends of the leg supports 27 connect and also hinge to the legs themselves. When in the legs opened position, the leg supports 27 have a slight negative incline. This incline is vital in that it makes it impossible to accidentally collapse the the legs. Any outside pressure on the legs wanting to push them in only increases the downward force of the control handle assembly, wanting to expand the legs outward even more, but limited by the inability of the control handle 24 to lower beyond the fixed upper leg support 28. The upper leg support casting 28, FIG. 4, is permanently attached to the lower section 13 of the invention. Each leg 23 is hinged within that casting and are allowed to swivel 45 degrees from a fully opened to a fully closed position.

Attached to the bottom of each leg is a double wheel caster 29 FIGS. 1, 2, and 3. The caster is fendered which minimizes corrosion and binding due to fluids and other matter dropping onto it. The use of four castered broadly spaced square tubular legs 23 with elevated leg supports 27, allows easy ambulation and minimizes the patient's foot involvement within the support structure of the invention.

Figure 10:
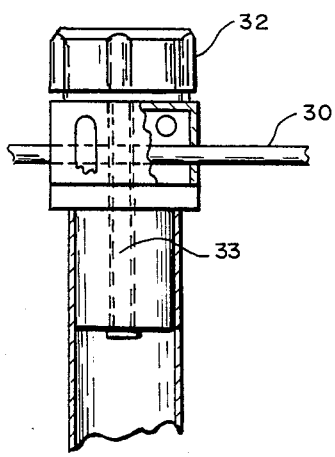
FIG. 10 is a fragmentary side cutaway perspective of the top hanger rod assembly.

An integral function of this invention is to be able to elevate and hang a variety of fluids used for enteral and parenteral feeding and infusion. To accomodate the fluid container (bag or bottle), a hanger rod assembly FIGS. 10 and 11 is attached to the top of the uppermost mast section 15. In this design, the hanger rods 30 are able to move horizontally with respect to the vertical mast, in an inward or outward motion. The ability to move permits the infusion fluid bag or bottle to be accurately positioned above the infusion pump or controller, and allows it to hang straight. Additionally, when the hanger rods 30 are positioned fully inward, the overall diameter and storage size of the invention is significantly reduced. The hanger rods themselves 30 are designed with a rams-horn end 31 so that any container hanging from them will not accidentally become disengaged from the hanging assembly.

The entire hanger assembly as viewed from the top FIG. 11 rotates on a 360 degree axis to ensure that the infusion line will not become wrapped around the pole as it is walked or when a telescoping lock and unlock procedure occurs which requires a 90 degree turn of any of the three mast sections.

A control knob 32 is used to secure rotational movement capability of the hanger assembly and to limit further movement of the hanger rods 30. The control knob 32 is attached to a bolt 33 which passes down through the hanger rod assembly and swivel bearing surface which allows rotation. As the knob and bolt are tightened, further movement of the hanger assembly and the hanger rods themselves is restricted.

While a preferred embodiment of the invention and a manner of making it has been shown and described, it is apparent that many modifications can be made without departing from the spirit and scope of the invention. Accordingly, the invention is not limited be the foregoing description, but is only limited by the scope of the claims.

What is claimed is:

1. A collapsible and fully portable medical I.V. equipment stand/pole of a character described above which comprises:
   a. a many sectioned mast assembly made from hollow tubes, with each being of a slightly larger diameter and the smallest being the uppermost tube and the largest being the lowermost, and each being able to slide smoothly within one another in a telescoping fashion;
   b. an internal pneumatic safety device built within the lower section of said tube mast assembly which acts to compress air as the upper sections of said mast assembly are lowered accidentally or on purpose thereby limiting the downward force and speed of said upper sections, but allowing movement of upper sections in both directions;
   c. a slidable control handle assembly which is mounted on the lower section of said mast assembly to which the lower leg supports a plurality of legs which support said mast assembly are connected via vertical rods and which allow for opening or closing of square tubular leg supports in one continuous motion;
   d. a hanger rod assembly which is permanently attached to the top of the uppermost said tubular section of said mast allowing independent inward and outward movement of each hanger rod and which rotates freely in either direction 360 degrees around the circumference of said uppermost tubular section and both movements of said hanger rod asembly which are free or able to be locked into position with the loosening or tightening of a vertically positioned control knob.

2. The invention described in claim 1 characterized in that a fixed upper leg support to which each upper leg is attached and allowed hinge movement, is permanently attached to the lower mast section.

3. An assembly as claimed in claim 1 wherein the control handle is a tubular sleeve long enough to accomodate a surrounding human hand, and which in a single motion is able to slide along the lowest section of said mast assembly while connected to four vertical rods whose other ends are attached to a floating lower collar to which is attached a lower leg support assembly, and which when moved downwardly in one continuous motion, causes said lower leg support assembly, including legs, to open outwardly and away from their closed position along the length of the lower mast section, with the horizontal leg supports achieving a negative incline which prohibits inward or collapsing movement of legs without intentional initiation of upward movement on said control handle.

4. An internal safety device built into lower section of said mast assembly as claimed in claim 1 comprising:
   a. a flexible seal mounted to the base of each of said upper sections which said sections telescope into said lower mast section;
   b. a check valve assembly permanently attached to the bottom of said lower mast section which allows air to pass into said mast assembly as the upper sections are extended, but which slowly bleeds air out of said lower section when the upper sections of said mast assembly are spontaneously lowered into the lower section of said mast assembly.

* * * * *